United States Patent [19]

Matson et al.

[11] Patent Number: 4,754,089

[45] Date of Patent: Jun. 28, 1988

[54] PHASE TRANSFER CATALYSIS

[75] Inventors: Stephen L. Matson, Harvard, Mass.; Thomas J. Stanley, Schnectady, N.Y.

[73] Assignee: Sepracor Inc., Marlborough, Mass.

[21] Appl. No.: 938,230

[22] Filed: Dec. 5, 1986

[51] Int. Cl.[4] .................... C07C 17/20; C07C 67/00; C07C 51/16; C07C 41/09

[52] U.S. Cl. ..................... 570/260; 260/684; 500/1; 502/544; 568/698

[58] Field of Search ......... 570/260; 562/544; 560/1; 260/684; 568/698

[56] References Cited

U.S. PATENT DOCUMENTS

2,642,920 2/1972 Johnson et al. ............... 570/260
3,641,172 2/1972 Johnson et al. ............... 570/260
3,923,914 12/1975 Kobetz et al. ............... 570/260
3,956,112 5/1976 Lee et al. ..................... 210/644
3,957,504 5/1976 Ho et al. ..................... 204/106
4,277,318 7/1981 Matlock et al. ............... 204/78
4,414,079 11/1983 Yamataka et al. ............ 549/295

Primary Examiner—J. E. Evans
Attorney, Agent, or Firm—Pennie & Edmonds

[57] ABSTRACT

The present invention relates to a novel method for conducting phase transfer catalysis in a multiphase reaction system wherein the different phases are separated by a membrane permeable to the phase transfer catalyst and its various reaction complexes. The invention also relates to membranes and a membrane-containing apparatus useful in carrying out phase transfer catalysis.

40 Claims, 7 Drawing Sheets

AQUEOUS

ORGANIC

* VERY SHALLOW FLOW CHANNELS
  0.05 CM x 10CM x 20 CM

* CHEMISTRY -
    BROMOOCTANE + I⁻ → IODOOCTANE + BR⁻
    ORGANIC SOLVENT - CHLOROBENZENE
    CATALYST - TETRABUTYLAMMONIUM IODIDE
    $K^{EQ} = 0.24$
    $K^{SEL} = 190$

* MEMBRANE
    GORETEX (W.L. GORE ASSOC., ELKTON, MD)
    NOMINAL THICKNESS    0.025CM
    POROSITY             61%
    TORTUOSITY           1.7

$RX + Y^- \dashrightarrow RY + X^-$

AQUEOUS

ORGANIC

ONLY GOES IN PRESENCE OF
PHASE-TRANSFER AGENT, $Q^+$ $Q^+$ = TETRAALKYL AMMONIUM OR
PHOSPHONIUM SALT
OR
CYCLIC POLYETHER
COMPLEXED WITH SMALL CATION

FIG. 1

$$Y^- + Q^+ \xrightleftharpoons[E^Y]{} [QY]$$

$$RX + [QY] \dashrightarrow RY + [QX]$$

$$[QX] \xrightleftharpoons[1/E^X]{} Q^+ + X^-$$

$$RX + [QY] \dashrightarrow RY + [QX]$$

ORGANIC

AQUEOUS  $X^- + Q^+Y^- \dashleftrightarrow Y^- + Q^+X^-$

CATALYST SELECTION CRITERIA

* $E^Y$ LARGE TO DRIVE CATALYST INTO ORGANIC PHASE
* $E^X$ SMALL TO DRIVE EXCHANGE OF $X^-$ FOR $Y^-$

FIG. 2

** REQUIRES DISPERSION
** REQUIRES COALESCENCE
    SURFACE ACTIVE CATALYST OR IMPURITIES
    CAUSE EMULSIFICATION        * TIME
       * ENERGY
       * CATALYST AND PRODUCT LOSS
          BY ENTRAINMENT

* VERY SHALLOW FLOW CHANNELS
   0.05 CM × 10 CM × 20 CM

* CHEMISTRY –
   BROMOOCTANE + $I^-$ → IODOOCTANE + $Br^-$
   ORGANIC SOLVENT – CHLOROBENZENE
   CATALYST – TETRABUTYLAMMONIUM IODIDE
   $K^{EQ} = 0.24$
   $K^{SEL} = 190$

* MEMBRANE
   GORETEX (W.L. GORE ASSOC., ELKTON, MD)
   NOMINAL THICKNESS  0.025 CM
   POROSITY  61%
   TORTUOSITY  1.7

PHASE TRANSFER CATALYSIS

BACKGROUND OF THE INVENTION

Phase-transfer catalysis is a technique for facilitating reactions between aqueous and organic phase reactants that normally do not proceed rapidly because neither reactant is soluble in the phase containing the other reactant. Often, the aqueous phase reactant is insoluble in the organic phase.

Typically, in phase transfer catalysis a phase transfer agent is added to a two-phase mixture to extract an aqueous-phase reactant into the organic phase so that a reaction can proceed. This technique has been exploited routinely by chemists for about ten to fifteen years as a tool for laboratory synthesis and, recently, the advantages of phase-transfer catalysts for industrial-scale production have been recognized. As a result, phase-transfer catalysis is now employed in the manufacture of many agricultural chemicals, pharmaceuticals, and other specialty chemicals and intermediates.

Phase-transfer catalysis may also be used where one of the coreactants has low water solubility. Often, phase-transfer catalysis will be used in reactions that occur in an organic media where two or more reactants are involved and all but one of these is soluble in the organic phase. The one insoluble reactant is usually an anion dissolved in an aqueous phase. In the absence of the phase transfer catalyst (otherwise known as "PTC"), the solubility of the anion in the organic phase is generally so small that negligible reaction rates are observed. However, the presence of a PTC in the reaction mixture promotes the transfer of the reacting anion into the organic phase, thus allowing the reaction to proceed at a significantly higher rate. Such organic reactants frequently will be structurally complex and are costly to manufacture. As an example, a number of the pyrethroid alpha-cyano esters are prepared by a phase-transfer-catalyzed coupling reaction between a substituted benzaldehyde moiety and a water-soluble cyanide salt, accompanied by reaction of the cyanohydrin so produced with a chrysanthemic acid derivative (typically an acyl halide). Baum, U.S. Pat. Nos. 4,254,050; 4,254,051; and 4,254,052.

Examples of general reaction classes amenable to phase transfer catalysis include nucleophilic substitution reactions, carbene formation, alkylations and alkoxylations, oxidations and reductions, and condensation, elimination, and addition reactions. More specifically, phase transfer catalysis can be used to catalyze the formation of ring compounds from straight-chain halocarbons, esters from acids, and ethers from alcohols; the synthesis of alkylchlorides and other alkyl halides by anion displacement; the alkylation of carbanions; and the oxidation of olefins to carboxylic acids. Freedman, H. H. (*Pure and Appl Chem.*, 58 (1986) 857–868) sets forth a compilation of reaction types and industrial applications of phase transfer catalysis.

Figure 3:
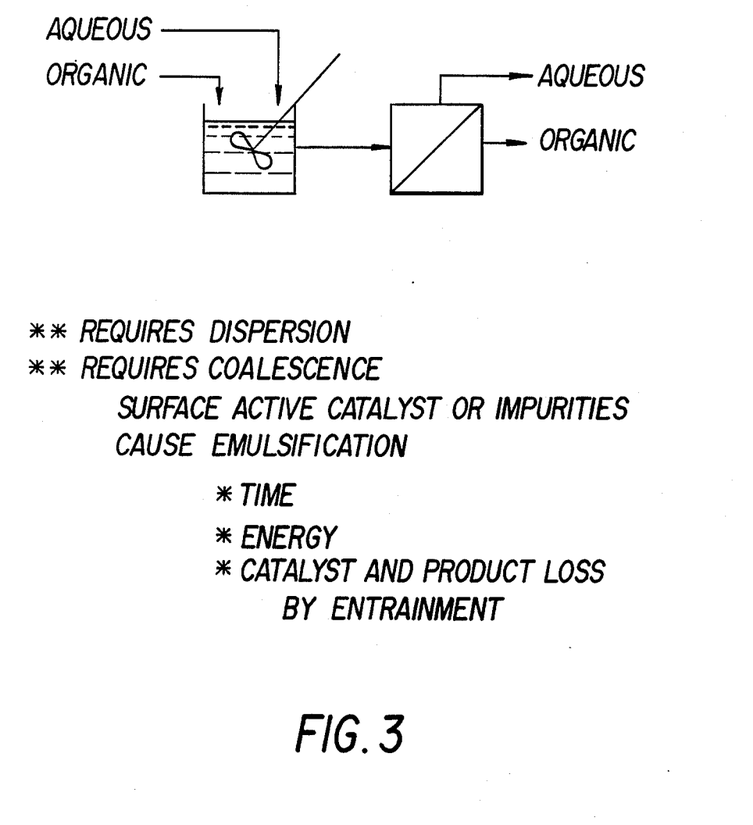
FIG. 3 schematically diagrams conventional phase transfer catalysis in a dispersed-phase system.

Conventionally, phase transfer catalysis is conducted in dispersed-phase systems wherein a two-phase mixture containing a phase transfer catalyst or PTC is stirred vigorously in a tank or other vessel to form an agitated interface or a dispersion (FIG. 3). Typically, the overall rate of conversion initially increases with stirring speed, since increasing the stirring speed causes the formation of greater numbers of smaller drops with higher interfacial areas. Ultimately, however, the conversion rate plateaus with increased stirring speed, as the heterogeneous reaction system undergoes a transition from mass-transfer control to bulk organic-phase kinetic control.

Unfortunately, a number of problems are associated with the small drop sizes required to maximize phase transfer catalysis reaction rates. In particular, some PTCs are surface-active by their very nature and act as effective emulsification agents. This is an advantage where dispersion and the creation of high interfacial areas are the objectives, but a disadvantage when it comes time for the phases to coalesce and be separated from one another. In addition to the practical difficulties associated with the continual making and breaking of dispersions and emulsions, and recovery of products therefrom, incomplete phase separation and entrainment of one phase into the other can result in loss of expensive product and phase transfer agent or PTC, as well as reduced product purity.

Other disadvantages of conducting phase transfer catalysis in dispersed-phase systems is its irreproducibility and relative inflexibility. For example, in conventional phase transfer catalysis, one is constrained to operate over relatively narrow ranges of volumetric phase ratios, and the relative mass transfer resistances of the aqueous and organic boundary layers cannot be readily and independently controlled. Scale-up of biphasic systems is often unreliable as well. With conventional dispersed-phase PTC processing there is relatively little way of independently manipulating boundary layer to bulk phase volume ratios, interfacial area to bulk phase volume ratios, and absolute and relative aqueous-phase and organic-phase mass transfer resistances in order to improve the efficiency of phase transfer catalysis.

Phase transfer catalysis has also been carried out with the use of ion exchange membranes serving as partitions in electrochemical diaphragm cells. U.S. Pat. No. 4,414,079 to Yamataka et al. and 4,277,318 to Matlock et al. Phase Transfer Catalysts have been covalently attached to capsule membranes which separate an aqueous phase outside of the capsule from an organic phase inside of the capsule. Once these capsules are formed, however, there is no way to provide fresh organic phase material to the inner portion of the capsule or continuously remove any product or reactant from that phase. Okahata et al., J. Chem. Soc., Chem. Comm., No. 13, pp. 920–922 (1985).

Figure 4:
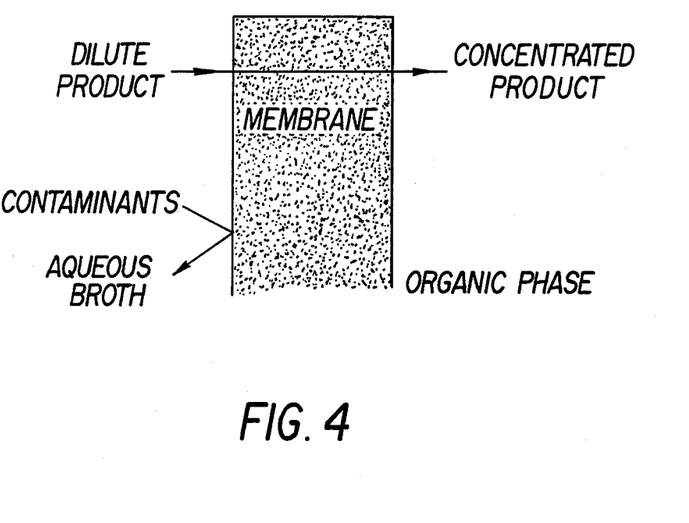
FIG. 4 illustrates the process of membrane solvent extraction.

The different phases of biphasic (i.e. aqueous/organic) systems have been separated with membranes, for instance, in the conduct of solvent extraction operations. (FIG. 4) U.S. Pat. Nos. 3,956,112 to Lee et al. and 3,957,504 to Ho et al. However, catalysis reactions are not disclosed as taking place during membrane solvent extractions.

Therefore, it is an object of the present invention to provide a method for carrying out phase transfer catalysis without the problems associated with mixing of dispersed phase systems and phase transfer catalysts.

It is a further object of this invention to enhance the separability of the phase components and reaction products after phase transfer catalysis.

It is an additional object of this invention to provide reliable, reproducible and controllable phase transfer catalysis which is capable of meeting the requirements of high-level industrial production.

SUMMARY OF THE INVENTION

Briefly stated, the present invention pertains to a method of carrying out phase transfer catalysis in a multi-phase system, such as with aqueous and organic phases, wherein the phases are separated by a membrane which membrane is substantially wet by one of the phases and wherein one of the phases contains at least one phase transfer catalyst. The membrane may be permeable to the phase transfer catalyst, the reactants in the different phases and reaction complexes with the phase transfer catalyst. In phase transfer catalysis, the reaction of these two solutes, each of which is initially present in separate and immiscible phases, is facilitated by the use of a reactant-complexing agent, the phase transfer catalyst or PTC. This invention encompasses the use of a phase transfer catalyst to accelerate, for instance, the rate of reaction of a water-soluble anionic reactant with organic-soluble reactants in a system containing two immiscible phases.

Figure 6:
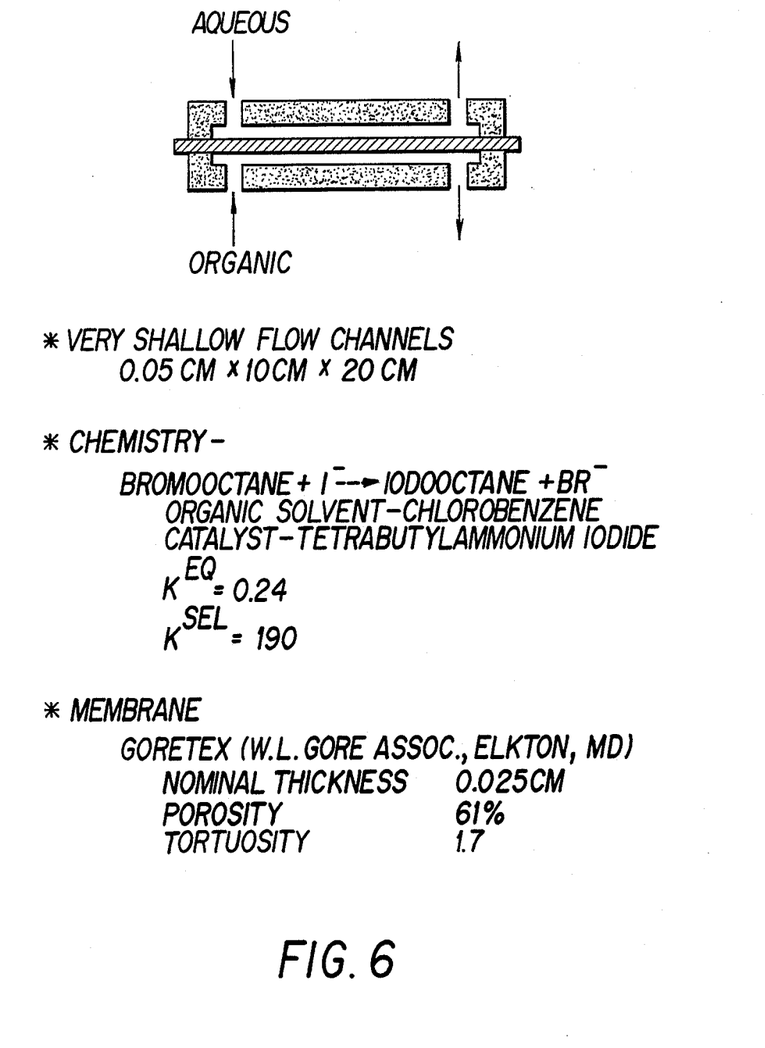
FIG. 6 illustrates a Phase Transfer Catalyst membrane reactor.

This invention is capable of being carried out using membranes having a variety of forms and configurations. For instance, the use of hollow-fiber and other types of membrane modules as two-phase contactors and reactors is particularly suited to and preferred in the conduct of phase-transfer-catalyzed reactions. (FIG. 6)

In particular, hollow-fiber membrane modules permit intimate, high-surface-area contact to be achieved between the immiscible phases on either side of the membrane, thereby obviating the need to disperse one phase in the other. As a result, entrainment and/or emulsification are minimized or eliminated, these problems otherwise being aggravated by the surface activity of certain phase transfer catalysts. Benefits accrue in terms of product recovery or yield, product purity, and, potentially, catalyst recovery and effectiveness. Additionally, membrane contacting equipment is simple, reliable, and relatively easily scaled-up as compared to other high-performance phase contacting/separating equipment such as centrifugal extractors. Finally, additional operating flexibility is gained in terms of the range of permissible organic:aqueous phase ratios or flow rate ratios.

BRIEF DESCRIPTION OF THE FIGURES

The present invention may be more readily understood by reference to the following figures wherein.

DETAILED DESCRIPTION OF THE INVENTION

The present invention is based, in part, upon the fact that certain compounds, such as organic quaternary salts of the elements of Group VA of the Periodic Table of the Elements (as in Handbook of Chemistry and Physics, Chemical Rubber Company, 45th Edition. (1964) p B2), can effectively catalyze heterogeneous reactions in which the reactants are located in distinct liquid phases by transferring ions or other reactive species across the phase interface. Frequently, the reaction of interest takes place in organic media and involves two or more reactants, one of which is insoluble in the organic phase. The one insoluble reactant is usually an anion dissolved in an aqueous phase which is in intimate contact with the organic phase. In the absence of the PTC the solubility of the anion in the organic phase is generally so small that negligible reaction rates are observed. However, the presence of a PTC in the reaction mixture promotes the transfer of the reacting anion into the organic phase and by this mechanism, the reaction is allowed to proceed at a significantly higher rate.

In general, phase transfer catalysts are cationic in nature, i.e., they are positively charged, and when in the presence of anions (negatively charged species) the two will form a neutral complex which is generally organic soluble. The degree to which the complex is soluble in the organic phase will depend, among other things, on the nature of the anion, the PTC, and the complex (sometimes called ion-pair), concentration of each species, temperature, and the volume of both the aqueous and organic phases. Many phase transfer catalysts are both water and organic soluble, but others are water insoluble and exist (e.g., chloride or hydroxide complexes) in organic media only. With the latter type of PTC, the extraction of anions from an aqueous phase generally takes place by an anion exchange mechanism at the organic/aqueous interface. Certain other PTCs, e.g. the polyethylene-glycols and crown ethers, are electrically neutral.

It should be noted that the nature of the organic phases generally employed in phase transfer catalysis usually results in two immiscible liquid phases, one organic and the other aqueous, which are characterized by a small but finite solubility of each phase within the other. Since the small amount of either phase dissolved in the other phase has no influence on the overall catalytic reaction process, such solvent-or water-saturated phases will be referred to as being "substantially free" of the other phase, thus denoting the absence of significant quantities of one water phase being dispersed or entrained within the other.

Broadly stated, the reaction involved in this invention provides a catalyst capable of complexing with a first reactant which is substantially disposed in a first liquid phase and transferring such first reactant into a second liquid phase which is substantially immiscible in the first phase, and which by this invention is separated from said first phase by a membrane, and there yielding up the first reactant to a second reactant which is substantially entirely disposed in such second liquid phase. More particularly, the type of reactions involved in this invention are those in which one or more reactants, usually but not always dissolved in inert solvent, are reacted with an anion dissolved in a second immiscible phase in the presence of a phase transfer catalyst. The PTC promotes the transfer of such anion into the first liquid phase which by this invention is separated from the second phase by a membrane.

This invention can also be generally stated to be a process for conducting heterogeneous reactions in a liquid-liquid two phase reaction system containing an organic phase and an aqueous phase, said reaction being carried out in the presence of reactants and a phase transfer catalyst, the improvement comprising separating said organic phase and aqueous phase with a membrane, which membrane is substantially wet by one of the phases and wherein one of the phases contains a phase transfer catalyst whereby said aqueous phase and organic phase remain substantially separated by said membrane during and after completion of said reaction.

Figure 1:
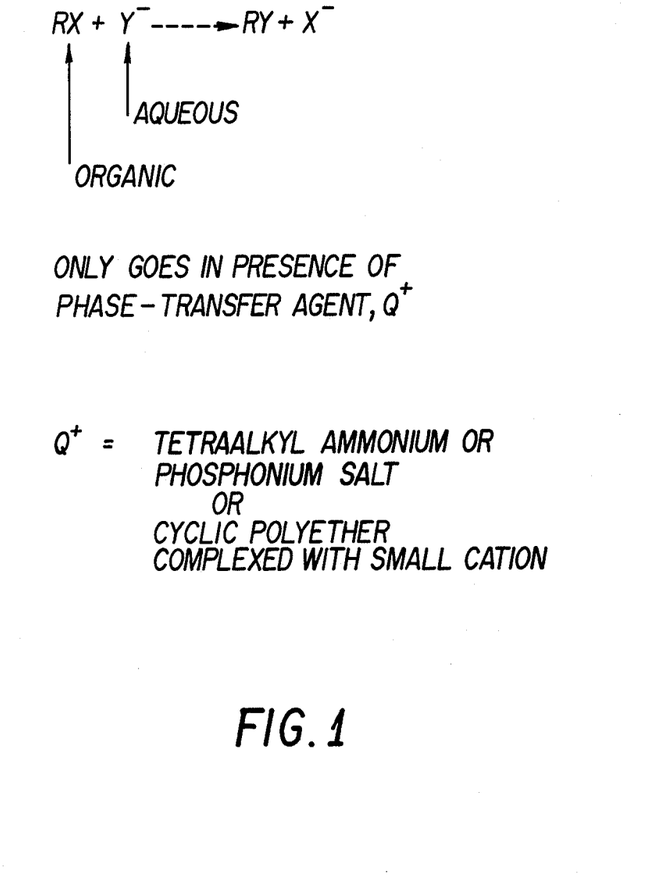
FIG. 1 illustrates a typical phase-transfer catalyzed reaction system.
Figure 2:
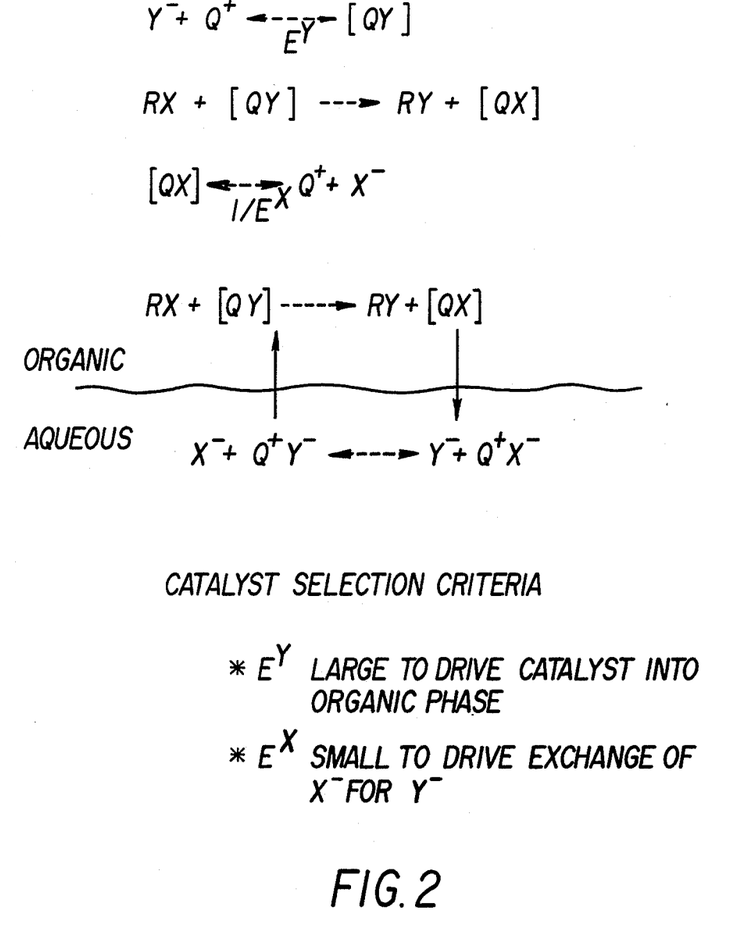
FIG. 2 illustrates the mechanism of phase transfer catalysis.

A typical PTC reaction of interest, a displacement reaction, is diagrammatically shown in FIG. 1. The mechanism of one type of phase-transfer reaction is shown in FIG. 2. As illustrated in FIG. 2, the catalyst "Q" extracts the aqueous phase reactant "Y" into the organic phase, where the reaction takes place between the complex "QY" and the reactant "RX". The products of this reaction are "RY" and the complex "QX". Reaction conditions are most favorable when extraction of "Y−" is highly favored over extraction of "X−" since this will cause the less soluble complex "QX" to be returned to the aqueous phase. This permits "Q+" to be regenerated and rendered capable of extracting more "Y−". Under these conditions, much less than stoichiometric quantities of catalyst can be used, because the catalyst can continually shuttle back and forth between phases, carrying fresh reactant into the organic phase with it. It is foreseeable in the practice of this invention that the phase transfer catalyst permeates, in both complexed and uncomplexed forms, into and within but not necessarily across the membranes on one side of the aqueous/organic interface. Certain phase transfer catalysts and complexes thereof used in the practice of this invention entirely cross the membrane from one bulk phase into the other, whereas other phase transfer catalysts and complexes will diffuse within but not completely cross the membrane. The term "permeate" as used herein is meant to describe and includes both of these modes of action, i.e., the phase transfer catalyst and its complexes both crossing the membrane and/or diffusing within it.

Typical and preferred phase-transfer catalysts utilized in carrying out this invention are quaternary ammonium or phosphonium cations, or cyclic polyethers complexed with small cations. It should be further pointed out that the terms catalytic activity and catalysis as they are here used are intended to mean that a finite increase in the rate at which the reactants in the two phases react with each other is caused to occur by the presence in the system of the phase transfer catalyst. Phase transfer catalysts may be obtained commercially from, for instance, the Henkel Corp. ("Aliquot 336-PTC" or tricaprylmethylammonium chloride, a water-insoluble quaternary ammonium salt); Ethyl Corp. ("TBMAC" or tri-n-butylmethylammonium chloride); American Cyanamid (organophosphine chemicals); Hexcel Specialty Chemicals (tetrabutylammonium and benzylalkylammonium salts); Petrarch Systems, Inc. (silacrown ethers) Bofors Nobel; and Air Products and Chemicals ("Dabco" or triethylene diamine). Still others include Union Carbide (PEG-600 or polyethyleneglycol); RSA Corp. (benzyltriethylammonium chloride and tetrabutylphosphonium chloride); and Sherex Chem. Corp. (Adogen-464 or tricaprylmethylammonium chloride).

In a preferred embodiment the phase transfer catalysis is carried out in a membrane reactor. In a further preferred embodiment, the membranes utilized in this reactor comprise hollow-fibers. In this embodiment hollow-fiber membrane modules permit intimate, high-surface-area contact to be achieved between the immiscible phases on either side of the membrane.

Additionally, this membrane contacting equipment is simple, passive, reliable, and relatively easily scaled-up as compared to other high-performance phase contacting/separating equipment such as centrifugal extractors. The use of this membrane contacting equipment in phase transfer catalysis should result in additional operating flexibility (e.g., organic: aqueous phase or flow rate ratios and continuous operation). Whereas in conventional phase transfer catalysis the interfacial area between the organic and aqueous phases depends on the relative volumes of the two liquid phases (as well as on other operating parameters such as the degree of agitation) in membrane phase transfer catalysis the area of the aqueous/organic interface is fixed and is equal to the membrane area. For this reason, membrane phase transfer catalysis reactors can efficiently be operated at more extreme volumetric phase or flow rate rations than is the case in the absence of a membrane. Indeed, it is forseeable within the scope of this invention that the volumetric flow rates of the two liquid-phases may differ by a factor of under 2 to more than 50 times the other.

Phase transfer catalysis "efficiency" criteria that are beneficially and positively effected by membrane reactor operation include reactor productivity (i.e., conversion rate per unit reactor volume), organic and aqueous phase stability (e.g., stability against emulsification), permissible organic-to-aqueous phase volume or flow rate ratios, product recovery and yield, product purity, catalyst recovery, and control over undesirable side reactions.

Figure 5:
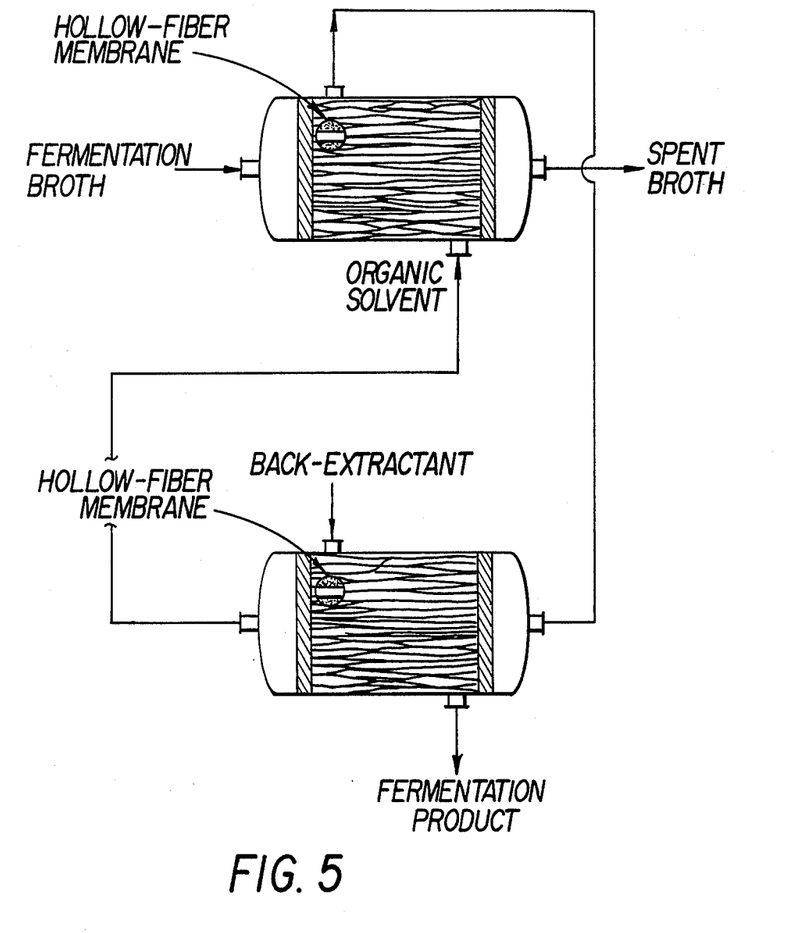
FIG. 5 illustrates membrane solvent extraction in a hollow-fiber membrane reactor.

Membranes and membrane modules suited to the practice of the present invention are similar construction to those used in membrane solvent extraction. (FIG. 5) Two types of membrane may be employed in the practice of this invention in, for instance, a phase contactor/separator reactor. The preferred membrane may be either a:

(1) hydrophobic and microporous membrane, or
(2) hydrophilic membrane, either gel-type or microporous.

Depending on their morphologies and composition many membranes will become wet upon contact with an aqueous or organic liquid. Without intending to be bound by any theory or mechanism, the term "wet" as used herein means that the membrane has been impregnated with a solvent from one of the two phases. For example, a membrane made of a hydrophobic material characterized by pores will generally become wet upon contact with an organic solvent due to capillary action. The same wetting properties are observed for membranes made of hydrophilic materials when contacted with an aqueous phase. On the other hand, many other membranes are substantially non-porous in the sense of being free of discrete, well-defined pores, i.e., the polymer phase (whether hydrophilic or hydrophobic) is substantially continuous in these membranes. However, this type of membrane will generally become swollen or wet when contacted with an appropriate solvent whenever a strong affinity exists between the polymer/solvent pair. One example of this type of membrane (also called "gel-type" membranes) is provided by regenerated cellulose membranes of the type used in hemodialysis, which swell markedly when placed in contact with water. Either type of membrane morphology (gel-type or microporous), or a combination thereof, when wet with the appropriate solvent (by capillarity or by swelling) can be used in the present invention.

In the preferred operation of the inventive method, an organic stream containing at least one of the reactants would be directed past one side of the membrane. Simultaneously, an aqueous stream containing at least one reactant (or coreactant e.g., an anionic reactant) would be directed across the opposite membrane surface. The phase in which the phase transfer catalyst is present in or will be introduced into the reactor will depend on the type of PTC employed (i.e., aqueous or organic soluble). For the case of water soluble PTCs, complex formation with the reactant anion will take place, followed by extraction of the complex into the organic phase. In the organic phase, the complex and organic soluble reactant(s) will react to form the desired products. Following the organic-phase reaction, the phase transfer catalyst complexed with one of the reaction products returns to the aqueous phase, dissociates, and, hence, is regenerated for participation in another reaction cycle.

When hydrophobic membranes are employed, either microporous or solvent swollen, the pressure difference across the membrane, defined here as the aqueous phase pressure minus the organic phase pressure, must be greater than zero throughout the reactor in order to prevent the organic phase from flowing through the membrane into the aqueous phase. On the other hand, when hydrophilic membranes are used, either gel-type or microporous, the pressure in the organic phase must be greater than the pressure in the aqueous phase throughout the reactor in order to prevent an ultrafiltrative flow of the aqueous phase into the organic phase. Typically, the pressure difference should be between 0.1 and 100 psi and usually between 1 and 10 psi. In any event, the transmembrane pressure difference should not exceed the value which would cause intrusion of the pressurized liquid phase into the membrane wet by the other liquid phase. In the case of microporous membranes, this intrusion pressure $\Delta P$ may be estimated from the Young-LaPlace equation as:

$$\Delta P = \frac{2\gamma}{r} \cos \theta$$

Where $\gamma$ is the liquid-liquid interfacial tension, r is the pore radius, and $\theta$ is the three-phase contact angle.

Typically, reactant conversions will depend on process stream flow rates or times of reaction, in addition to the particular phase transfer catalyst and membrane used in the process. Knowledge of PTC-catalyzed reaction kinetics and membrane permabilities will assist in optimizing such reactor operating conditions as process stream flow rates and reaction times. In the practice of this invention, phase-transfer-catalyzed reaction rates will typically increase with temperature, as they do in the absence of a membrane, with absolute operating pressure levels having an insignificant effect. However, one of the significant advantages of this invention is the ability to operate over a wide range of flow rates, temperature, volumetric phase or flow rate ratios, reactant compositions, and with differing membranes and phase transfer agents.

Generally speaking, either hydrophobic or hydrophilic membrane materials may be used in the practice of the present invention. Similarly, both microporous and solvent-swollen (e.g., gel-type) membrane morphologies will exhibit significant permeability to many PTCs and their complexes with reactants and products, and so will be suitable for the practice of this invention. However, whereas most of the alkyl and benzylammonium salts are small species with molecular weights (MWs) ranging from about 200 to 400 (e.g., "BTEAC" or benzyltriethylammonium chloride, MW 228; Aliquot-336/Adogen-464 or tricaprylmethyl-ammonium chloride, MW 400), certain of the polyethylene glycols (PEGs) employed as phase transfer catalysts have molecular weights ranging from about 350-600 to as much as several thousand. With large or bulky PTCs (e.g., the higher-molecular-weight PEGs), microporous membranes may be preferred to solvent-swollen gel-type membranes for reasons of the generally higher permeability of the microporous membranes large species.

When hydrophobic membranes are employed, either microporous or solvent swollen, the aqueous/organic interface will be located at the surface of the membrane adjacent to the aqueous stream. The membrane itself will be substantially wet by and will therefore contain organic solvent, and the PTC-catalyzed reaction will occur in part within the membrane proper, as well as within the bulk organic phase on one side of the membrane. In contrast, when the membrane is hydrophilic, whether gel-type or microporous, the aqueous/organic interface will reside at the surface of the membrane adjacent to the organic stream, and the reaction will take place primarily in the organic phase on one side of the water-wet membrane. In either case, the membrane will be appreciably permeable to at least one of the reactants and to the phase transfer catalyst.

Examples of the method according to this invention are given hereafter. These examples are meant to be illustrative and not to be considered as limiting the scope of the invention.

EXAMPLE 1

A flat sheet membrane reactor was fashioned from an alumimum block (FIG. 6). A flow channel 0.05 cm deep, 10 cm wide, and 20 cm long was cut into each block. Inlet and outlet flow distribution manifolds were also machined into the blocks. The flowing streams were isolated by bolting the two blocks together with a hydrophobic membrane sandwiched in between. The aqueous stream was run at a higher pressure than the organic stream in order to maintain a stable aqueous/organic interface at the surface of the hydrphobic membrane adjacent to the aqueous stream. Because of this pressure drop, the membrane was supported separately. A highly porous stainles steel screen 0.05 cm thick was fastened to the bottom of the organic stream flow channel to provide this support.

A reaction using the above reactor was conducted using the following chemistry. Bromooctane in the organic solvent chlorobenzene was reacted with aqueous iodide to form iodoctane in chlorobenzene and aqueous bromide ion. To ensure that this reaction required the use of a phase transfer catalyst, a brief dispersed-phase study was conducted. A solution 0.5 M in bromooctane and 0.1 M in tetradecane (as a gas chromatograph standard) in chlorobenzene was stirred with an equal volume of 2.0 M potassium iodide at 40 degrees C. for 4 hours. After this period, no iodooctane could be detected by gas chromatography. All analyses were conducted with a Perkin-Elmer 3920 gas chromatograph equipped with a flame ionization detector and a 10′ by ⅛″ OV-101 column at 200 degrees C. When this experiment was repeated using 0.05 M tetrabutylammonium bromide in the organic feed as a phase transfer catalyst, 50% conversion of bromooctane to iodoctane was observed after 4 hours. Because the organic-phase concentration of tetrabutylammonium iodide, the active form of the catalyst, remains constant with time under these reaction conditions, first-order kinetics with respect to the disappearance of bromooctane is predicted by the phase transfer catalysis mechanism. This effect was observed in these experiments.

In the membrane reactor experiments, the feed compositions were the same as in the above dispersed-phase experiments. The membrane material used was Goretex 10-mil tape supplied by W.L. Gore Associates, Elkton, Md. Goretex is a microporous polytetrafluoroethylene membrane. The porosity and tortuosity were measured at 61% and 1.7, respectively. Flow rates were set using constant head tanks. The requisite membrane pressure drop was maintained by elevating the aqueous stream tube outlet several inches above the organic tube outlet.

The aluminum reactor was maintained at 40 degrees C. in a constant temperature bath. The flowrates, always equal to each other, were varied in the range of 3 to 8 ml/hr. After each adjustment, a period of at least 5 hours and usually overnight was allowed for the system to reach steady state. Several measurements of conversion were taken during a period of 2 to 3 hours to ensure that steady state had been achieved. The steady state experimental results were as follows: 33% conversion at 3.1 ml/hr., 22% conversion at 4.4 ml/hr, and 16% conversion at 7.1 ml/hr. No entrainment of chlorobenzene in the aqueous effluent could be detected visually, and only a slight trace was found by GC analysis. No water was observed in the chlorobenzene effluent. The reactor operated for 72 hours without interruption.

EXAMPLE 2

In the example set forth below, the initial organic-and aqueous-phase feed compositions were the same as used in Example 1. The membrane employed was gel-type regenerated cellulose in a hollow-fiber geometry, with the organic phase fed to the lumen side of the fibers and the aqueous phase fed to the shell side of the module. The hollow-fiber module contained 1.5m$^2$ of active membrane area characterized by an ultrafiltration rate of 6.4 ml/hr-mmHg and by urea, creatinine, and vitamin B$_{12}$ clearances of 183, 165 and 59 ml/min, respectively, as measured at blood ($Q_B$) and dialysate ($Q_D$) flow rates of $Q_B=200$ ml/min and $Q_D=500$ ml/min. The hollow-fiber membrane module, designated AM-300M, was obtained from Asahi Medical Co. via Mediflex International, Inc. In order to impart some limited degree of solvent resistance to the modules, the dialyzer end caps were first coated with Devcon 5-minute epoxy, and the original O-rings were replaced with more solvent-resistant Viton O-rings.

The initial volumes of organic and aqueous phases charged to the system were both 250 ml, and both phases were recirculated between the membrane module and their respective reservoirs at flow rates of 5 ml/min. The reaction temperature was maintained at about 38° C. by immersing the module in a thermostated water bath, and bromooctane conversion was followed as a function of time by gas chromatography.

Figure 7:
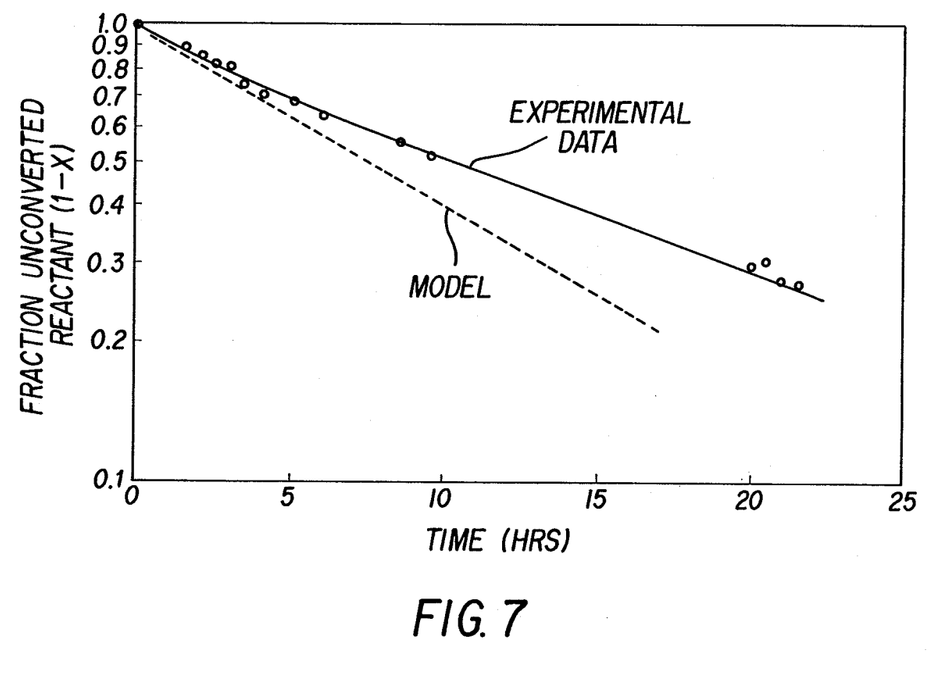
FIG. 7 graphically shows a semilog plot of reactant removal vs. time in a membrane reactor.

Conversion vs. time data are summarized in Table I. These data are also plotted in conventional fashion on semi-logarithmic coordinates in 7. From the slope of the solid line through the data, a first-order rate constant $k_1$ of 0.09 hr$^{-1}$ can be calculated. Also shown for comparison (as the dashed line) is the conversion vs. time prediction of an analytical model for the case of ion-exchange equilibrium where the mass transfer resistances on both sides of the membrane are assumed negligible.

TABLE I

| Bromooctane Conversion vs. Time in a Phase-Transfer-Catalyzed Membrane Reactor | |
|---|---|
| Time (hrs) | Reactant Conversion |
| 0.00 | |
| 1.5 | 0.11 |
| 2.0 | 0.15 |
| 2.5 | 0.17 |
| 3.0 | 0.19 |
| 3.5 | 0.24 |
| 4.0 | 0.29 |
| 5.0 | 0.32 |
| 6.0 | 0.36 |
| 8.5 | 0.43 |
| 9.5 | 0.48 |
| 20.0 | 0.70 |
| 20.5 | 0.69 |
| 21.0 | 0.72 |
| 21.5 | 0.73 |
| 21.5 | 0.72 |

The present invention is not intended to be limited in scope by the above experiments or by the membranes or phase transfer catalysts used since each is intended merely as an illustration of the invention. In addition, any membrane or phase transfer catalyst which is functionally equivalent to those set forth herein is intended to be within the scope of this invention. Indeed, various modifications of the invention, in addition to those shown and described herein, will become apparent to those skilled in the art from the foregoing description and accompanying s. Such modifications are intended to fall within the scope of the appended claims.

We claim:

1. A process for conducting heterogeneous reactions in a liquid-liquid two phase reaction system containing an organic phase and an aqueous phase, said reaction being carried out in the presence of reactants and a phase transfer catalyst, the improvement comprising:
    (a) separating said organic phase and aqueous phase with a membrane, which membrane is substantially wet by one of the phases and wherein one of the phases contains a phase transfer catalyst
whereby said aqueous phase and organic phase remain substantially separated by said membrane during and after completion of said reaction.

2. The process of claim 1 wherein said membrane is of a hydrophilic material.

3. The process of claim 1 wherein the membrane is of a hydrophobic material.

4. The process of claim 2 wherein said hydrophilic membrane is one selected from the group consisting of regenerated cellulose, hydrophilic polyacrylonitrile-based copolymer, and polyethersulfone/polyethylene oxide polymer blend.

5. The process of claim 3 wherein said membrane is one selected from the group consisting of polytetrafluoroethylene, polysulfone, polyethersulfone, poly-(2,6-dimethyl) phenylene oxide, polypropylene, polypropylene/polybutadiene polymer blends, and polyvinylidene fluoride.

6. The process of claim 1 wherein the two-phase reaction is selected from the group consisting of a displacement reaction, an alkylation reaction, an oxidation reaction, or an esterification reaction.

7. The process of claim 1 wherein the membrane separates a reaction chamber into two reaction chambers.

8. The process of claim 7 wherein the aqueous phase and organic phase are located in opposite chambers.

9. The process of claim 1 wherein the membrane is in the form of a hollow fiber.

10. The process of claim 9 wherein multiple hollow fibers are placed together in a membrane reactor, the bulk aqueous phase is located within the bores of the hollow fibers, the organic phase is located outside of the fibers, and one of said phases wets said membrane.

11. The process of claim 9 wherein multiple hollow fibers are placed together in a membrane reactor, the organic phase is located within the bores of the hollow fibers, the bulk aqueous phase is located outside of the fibers, and one of said liquid phases wets said membrane.

12. The process of claim 1 wherein the membrane is in the form of a flat sheet.

13. The process of claim 1 wherein the phase transfer catalyst is one selected from the group consisting of quaternary ammonium cations, quaternary phosphonium cations, and cyclic polyethers.

14. The process of claim 1 wherein the phase transfer catalyst is tricaprylmethylammonium chloride.

15. The process of claim 1 wherein at least one of said phases is continuously flowing along the surface of said membrane.

16. The process of claim 15 wherein one of said reactants is present in said aqueous phase said reactant being contacted with one surface of said membrane and the other of said reactants is present in said organic phase said reactant being contacted with the opposite surface of said membrane.

17. The process of claim 15 wherein at least one reaction product is removed from one of said phases.

18. The process of claim 1 wherein said aqueous and organic phases are flowing in opposite directions along the opposite surfaces of said membrane.

19. The process of claim 1 wherein the phase transfer catalyst is tri-n-butylmethylammonium chloride.

20. The process of claim 1 wherein the phase transfer catalyst is an organophosphine.

21. The process of claim 1 wherein the phase transfer catalyst is a benzylalkylammonium salt.

22. The process of claim 1 wherein the phase transfer catalyst is one selected from the group consisting of a cyclic polyether, a polyethlene glycol, and a silacrown ether.

23. The process of claim 1 wherein the membrane is substantially wet by the aqueous phase and the organic phase is maintained at a pressure in excess of the pressure on the aqueous phase.

24. The process of claim 23 wherein the organic-phase pressure is maintained from 0.1 psi to 100 psi higher than that of the aqueous phase.

25. The process of claim 24 wherein the organic-phase pressure exceeds that of the aqueous phase by 1 to 20 psi.

26. The process of claim 1 wherein the membrane is substantially wet by the organic phase and the aqueous phase is maintained at a pressure in excess of the pressure on the organic phase.

27. The process of claim 26 wherein the membrane is substantially wet by the organic phase and the aqueous phase is maintained at a pressure in excess of the pressure on the organic phase.

28. The process of claim 27 wherein the aqueous-phase pressure exceeds that of the organic phase by a 1 to 20 psi.

29. The process of claim 1 wherein the membrane is substantially non-porous and swollen by one of said phases.

30. The process of claim 1 wherein the membrane is porous and wet by one of said phases.

31. The procless of claim 1 wherein the volumetric flow rates of the two liquid phases differ by a factor ranging from two to fifty.

32. The process of claim 1 wherein the phase transfer catalyst is selected from the group consisting of a tetrabutyl phosphonium salt and a alkylphosphonium salt.

33. The process of claim 1 wherein the phase transfer catalyst is triethylene diamine.

34. The process of claim 1 wherein at least one of said reactants is dissolved in the organic phase and another of said reactants is an anionic reactant which is dissolved in the aqueous phase.

35. The process of claim 34 wherein said membrane is substantially wet by one of the phases and is substantially permeable to said phase transfer catalyst, the complex formed between said phase transfer catalyst and the anionic reactant, and the complex formed between said phase transfer catalyst and a product of said heterogeneous reaction.

36. The process of claim 1 wherein said phase transfer catalyst is soluble in said organic phase and substantially insoluble in said aqueous phase.

37. The process of claim 36 wherein said membrane is wet by the aqueous phase.

38. The process of claim 37 wherein said phase transfer catalyst complexes at the interface between said aqueous and organic phases with one of said reactants which is present in said aqueous phase.

39. The process of claim 1 wherein the membrane is substantially permeable to said phase transfer catalyst, the complex formed between said phase transfer catalyst and one of said reactants and the complex formed between said phase transfer catalyst and the product of said heterogeneous reaction.

40. The process of claim 1 wherein said phase transfer catalyst permeates said membrane.

* * * * *